United States Patent
Lange et al.

(10) Patent No.: US 8,705,027 B2
(45) Date of Patent: Apr. 22, 2014

(54) OPTICAL DEFECT AMPLIFICATION FOR IMPROVED SENSITIVITY ON PATTERNED LAYERS

(75) Inventors: Steven R. Lange, Alamo, CA (US);
Stephane Durant, Biarritz (FR);
Gregory L. Kirk, Pleasanton, CA (US);
Robert M. Danen, Pleasanton, CA (US);
Prashant Aji, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 39 days.

(21) Appl. No.: 13/384,330

(22) PCT Filed: Jul. 15, 2010

(86) PCT No.: PCT/US2010/042148
§ 371 (c)(1),
(2), (4) Date: Jan. 16, 2012

(87) PCT Pub. No.: WO2011/008964
PCT Pub. Date: Jan. 20, 2011

(65) Prior Publication Data
US 2012/0113416 A1 May 10, 2012

Related U.S. Application Data

(60) Provisional application No. 61/226,260, filed on Jul. 16, 2009.

(51) Int. Cl.
*G01N 21/00* (2006.01)

(52) U.S. Cl.
USPC .................................. 356/237.5; 356/237.4

(58) Field of Classification Search
USPC ................... 356/326, 237.1–237.6, 632, 388, 356/300–301, 239.8, 430–431, 317, 311; 250/559.4, 559.01, 221, 216, 559.04, 250/359.1; 438/7, 8, 14, 694, 15, 16; 427/10, 8, 9
See application file for complete search history.

(56) References Cited

U.S. PATENT DOCUMENTS

| | | | |
|---|---|---|---|
| 6,352,803 B1 | 3/2002 | Tong et al. | |
| 6,603,529 B1 * | 8/2003 | Finarov | 355/27 |
| 2003/0227617 A1 | 12/2003 | Yoshida et al. | |
| 2006/0114463 A1 | 6/2006 | Detinkin et al. | |
| 2006/0192904 A1 | 8/2006 | Almogy et al. | |
| 2008/0006786 A1 | 1/2008 | Williamson et al. | |
| 2008/0225286 A1 | 9/2008 | Shibata et al. | |
| 2008/0311283 A1 | 12/2008 | Brasack et al. | |
| 2008/0318139 A1 | 12/2008 | Dersch et al. | |

* cited by examiner

Primary Examiner — Tri T Ton
(74) Attorney, Agent, or Firm — Suiter Swantz pc llo

(57) ABSTRACT

A method for wafer defect inspection may include, but is not limited to: providing an inspection target; applying at least one defect inspection enhancement to the inspection target; illuminating the inspection target including the at least one inspection enhancement to generate one or more inspection signals associated with one or more features of the inspection target; detecting the inspection signals; and generating one or more inspection parameters from the inspection signals. An inspection target may include, but is not limited to: at least one inspection layer; and at least one inspection enhancement layer.

16 Claims, 11 Drawing Sheets

| 30nm DR | DF | BF |
|---|---|---|
| PR baseline | 2.51 | 6.64 |
| Ag | 1.19 | 23.60 |
| Al | 6.57 | 30.00 |
| Au | 2.38 | 24.40 |
| TaN | 4.44 | 38.20 |
| TiN | 3.88 | 15.15 |
| 20nm DR | DF | BF |
| PR Baseline | 0.41 | 2.85 |
| Ag | 1.56 | 8.92 |
| Al | 1.26 | 14.50 |

FIG. 3

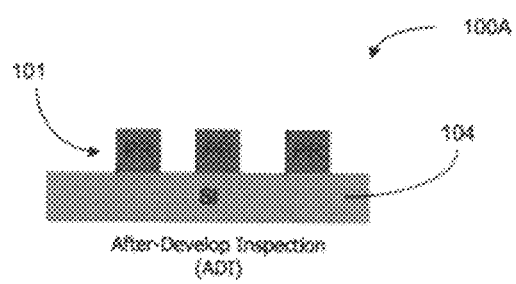
FIG. 8A
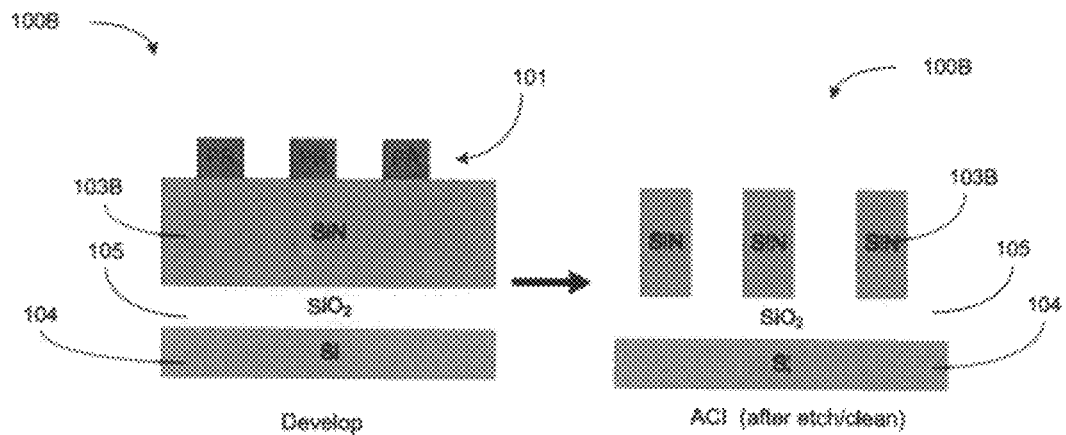
FIG. 8B        FIG. 8C

OPTICAL DEFECT AMPLIFICATION FOR IMPROVED SENSITIVITY ON PATTERNED LAYERS

RELATED APPLICATIONS

This application claims priority to Patent Cooperation Treaty Application No. PCT/US10/42148 filed on Jul. 15, 2010 which claims priority to U.S. Provisional Application Ser. No. 61/226,260 filed on Jul. 16, 2009, all of which are hereby incorporated by reference in their entirety.

BACKGROUND

This invention deals with improving the sensitivity of defect inspection on patterned surfaces where the patterned structures are not fabricated as intended. The inspection of these surfaces may involve directing light onto such surfaces, collecting light from the surface and processing the collected light to determine whether defects are present. An example of this can be in semiconductor wafer manufacturing where thin-film layers are processed with lithography creating patterns in the surface that are subsequently etched and processed to create semiconductor devices. In the lithography process, a layer of photoresist is deposited on the surface and the photoresist is illuminated with a pattern that is developed and processed to establish a pattern that will be etched into the surface to create a layer for the semiconductor device. Defects within photoresist layers are an example of low-signal producing defects where some amplification of detection signals may be required to adequately identify defects. This need may be higher when considering the extreme ultraviolet (EUV) lithography requirements for detecting printed defects from the mask. Prior methods for accounting for low level signals included optimization of the inspection parameters of light, spectral band, aperture mode and tool speed/pixel to identify an optimal inspection recipe.

However, such optimizations may be insufficient for detecting signal levels on print-check wafers (sometimes called "flop-down wafers") resulting from ever-smaller defects in future design rules (DR) (e.g. a 15 nm DR having allowed excursions of 1/10 of the line width or 1.5 nm) established from EUV mask inspection requirements.

SUMMARY

A method for wafer defect inspection may include, but is not limited to: providing an inspection target; applying at least one defect inspection enhancement to the inspection target; illuminating the inspection target including the at least one inspection enhancement to generate one or more inspection signals associated with one or more features of the inspection target; detecting the inspection signals; and generating one or more inspection parameters from the inspection signals.

It is to be understood that both the foregoing general description and the following detailed description may be exemplary and explanatory only and may be not necessarily restrictive of the invention as claimed. The accompanying drawings, which may be incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which Figure Number:

FIG. 3 shows signal values using the best inspection band/mode recipe for various inspection enhancement layers;

FIG. 8 shows a process for pattern transfer of one inspection target layer into another inspection target material;

DETAILED DESCRIPTION OF THE INVENTION

Figure 1:
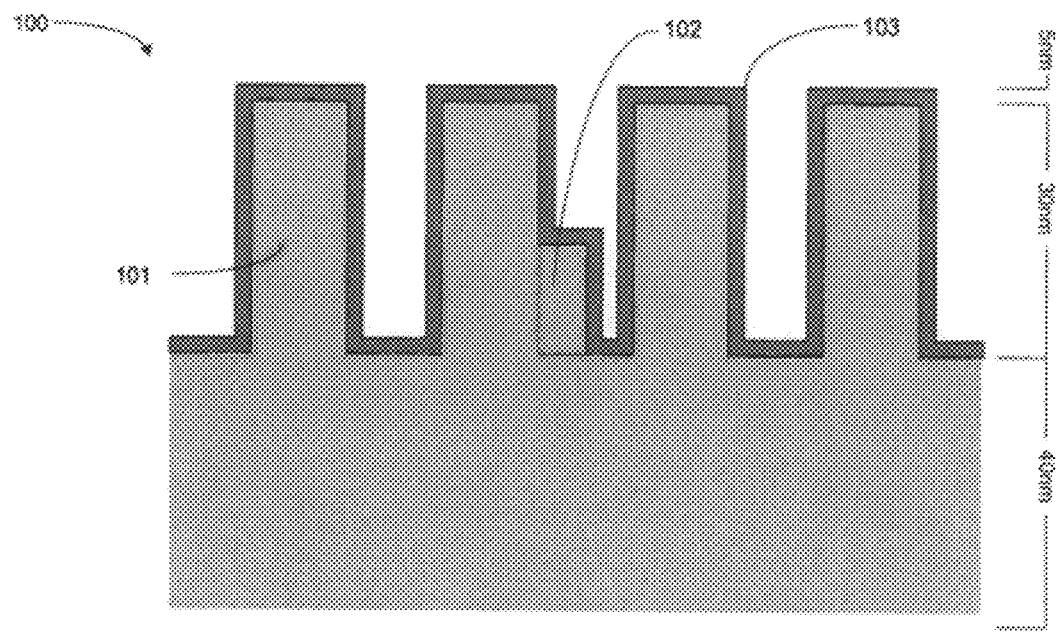
FIG. 1 shows a cross-sectional profile of a wafer surface with a periodic structure and a defect.

In the following detailed description of exemplary embodiments, reference is made to the accompanying drawings, which form a part hereof. In the several figures, like referenced numerals identify like elements. The detailed description and the drawings illustrate exemplary embodiments. Other embodiments may be utilized, and other changes may be made, without departing from the spirit or scope of the subject matter presented here. The following detailed description is therefore not to be taken in a limiting sense, and the scope of the claimed subject matter is defined by the appended claims.

Brightfield microscopes (e.g. a 2830 Brightfield Patterned Wafer Defect Inspection System produced by KLA-Tencor Corporation, Milpitas, Calif.) may be employed to image the wafer's surface. Such devices may operate in several modes including: (1) brightfield mode where the specular reflection from a surface of an inspection target and any propagating diffraction modes that returned to the microscope aperture may be captured thereby measuring the loss via signal inspection that it is not returned to the microscope; (2), unresolved dark-field (DF) mode where the wafer's surface is imaged and scattered light from the defect and scattered signals from random noise events are captured; and (3) resolved DF where an image of the wafer's surface may contain both scattered light from the defect as well as diffracted orders from the structure.

It may be the case that a number of layers may be difficult to inspect using because the materials may produce small signals (e.g. lithography layers where photoresist is a poor scatterer of light). Additionally, defects are getting smaller as lithography tools advance their capabilities to allow smaller patterns to be created making inspection of such layers even more challenging because smaller defects generally produce less signal than larger defects.

Recent improvements in EUV lithography indicate that it might be a viable option for future generations of lithography. Detection of phase defects, caused by either bumps and/or holes in the substrate or particles deposited during multilayer coatings needed to make the substrate reflecting at the EUV wavelength is important to the development of defect-free masks. Defect free masks are needed so that mask defects do not propagate into the photoresist and resulting in defective semiconductor devices. However, masks and mask substrates for the EUV process are opaque to UV and visible wavelengths. In such cases, actinic (EUV wavelength) inspection may be required to be sensitive to these defects. However, if an exposed and developed photoresist wafer could be inspected with enough sensitivity to detect all the defects resulting from the mask, it may serve satisfy the requirements for qualification and recertification of the EUV mask itself.

Another candidate for next generation lithography may be nano-imprint lithography (NIL) which uses a multiple-use template that may be pressed into the photoresist establishing a pattern in photoresist. Again, having a wafer inspection tool with sufficient sensitivity to qualify the NIL mask through inspection of a resulting printed wafer may be more attractive than building a dedicated tool to inspect the parent and child NIL molds.

The below described invention provides methods of enhancing resultant signals produced from wafer layers of an inspection target (i.e. "inspection layers") subject to optical defect inspection which have a low signal response (e.g. photoresist layers). For example, one or more inspection enhancements may be applied to an inspection target to enhance the detectability of defects in various inspection layers of that inspection target. For example, as described below, an inspection enhancement may include at least one of an application of an topical inspection enhancement layer over an inspection layer, an application of an inspection enhancement underlayer beneath an inspection layer, transfer of a patterned layer of the inspection target to an inspection enhancement layer of a second inspection target and/or selection of inspection layer materials exhibiting particular optical properties.

Following application of an inspection enhancement to an inspection target, the inspection target may be subjected to inspection by an inspection tool. For example, an inspection tool (e.g. a 2830 Brightfield Patterned Wafer Defect Inspection System produced by KLA-Tencor Corporation, Milpitas, Calif.) may be used to illuminate an inspection target which as been subjected to an inspection enhancement with electromagnetic radiation across various spectral bands to generate one or more inspection signals (e.g. reflected signals, scattered signals, and the like) associated with one or more physical features of the inspection target. Those inspection signals may be detected by the inspection tool and analyzed to produce one or more inspection parameters indicative of the physical features of the inspection target.

Reference will now be made in detail to the subject matter disclosed, which is illustrated in the accompanying drawings.

For example, FIG. 1 shows a cross-sectional view of an inspection target 100 patterned to include a line-space array of parallel lines. The inspection target 100 may include an inspection layer 101 (e.g. a photoresist layer subject to inspection) including one or more defect structures 102, to which a topical inspection enhancement layer 103A may be applied. The topical inspection enhancement layer 103A may have increased inspection properties relative to the inspection layer 101 (e.g. enhanced reflectivity, scattering, refractive index, etc.). The application can be done with a deposition tool such as a chemical vapor deposition process. The increased scattering capabilities of the topical inspection enhancement layer 103A may enhance the scattering signal due to its material properties. For example, a metallic defect will scatter much more light than a dielectric defect. Such a topical inspection enhancement layer 103A may also serve to increase the volume of a particular defect, thereby further increasing the scattering associated with that defect.

Figure 2A:
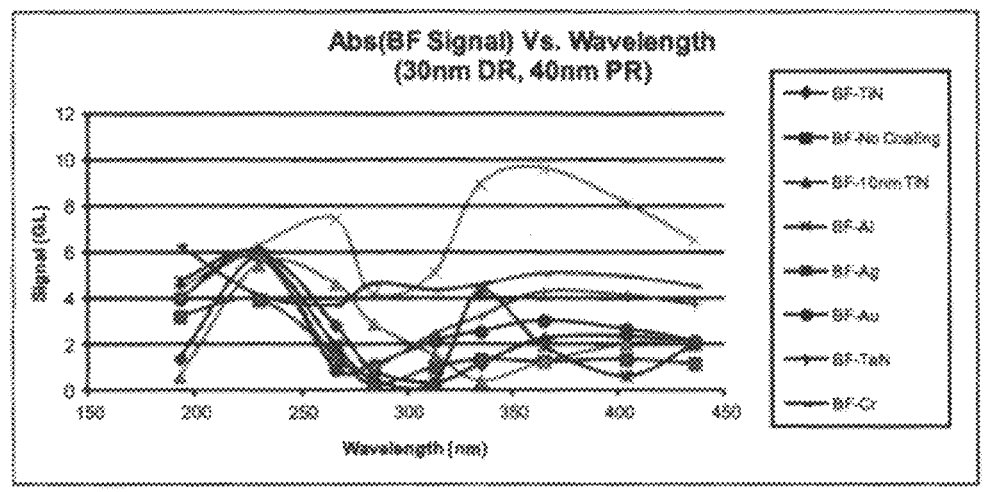
FIG. 2A shows signal responses for an inspection system operating in a brightfield mode as a function of wavelength for various defect inspection enhancement layer materials.
Figure 2B:
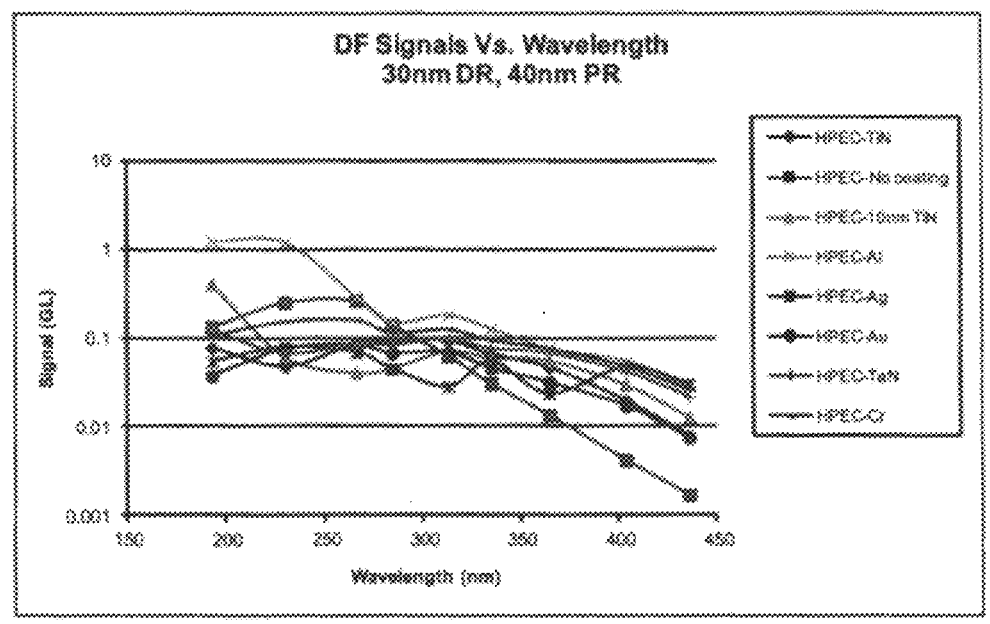
FIG. 2B shows signal responses for an inspection system operating in a darkfield mode as a function of wavelength for various inspection enhancement layer materials.

Various materials may be used to coat a wafer to provide a topical inspection enhancement layer 103A. Referring to FIGS. 2A and 2B, representative scattering signals using various topical inspection enhancement layer 103A materials are shown. For example, materials incorporated into the topical inspection enhancement layer 103A may include, but are not limited to titanium nitride, aluminum, silver, gold, tantalum nitride and/or chromium. It should be noted that some topical inspection enhancement layer 103A materials may include those that are commonly used in wafer fabrication processes for other purposes (e.g. adhesion layers). FIGS. 2A and 2B show the respective signals (e.g. in gray levels (GL) out of a possible 255) produced from a full-height bridge-type defect using a darkfield (DF) mode (HPEC) and a brightfield (BF) mode on a 2830 Brightfield Patterned Wafer Defect Inspection System produced by KLA-Tencor Corporation, Milpitas, Calif., for an inspection target having a 5 nm coating of inspection enhancement material over a 30 nm DR NIL structure with a 40 nm depth photoresist (e.g. as shown in FIG. 1) as a function of the inspection wavelength. As shown, aluminum provides signal enhancement in both DF and BF that increases associated defect signals above the uncoated case.

Using the simulated wavelength data, wafer inspection tool parameters may be analyzed to determine how a wafer inspection tool's signal can be improved. FIG. 3 shows signals in BF and DF for the 2830 Brightfield Patterned Wafer Defect Inspection System produced by KLA-Tencor Corporation, Milpitas, Calif., using the inspection recipe for the various topical inspection enhancement layer 103A materials optimized to result in the maximum signal responses.

Figure 4A:
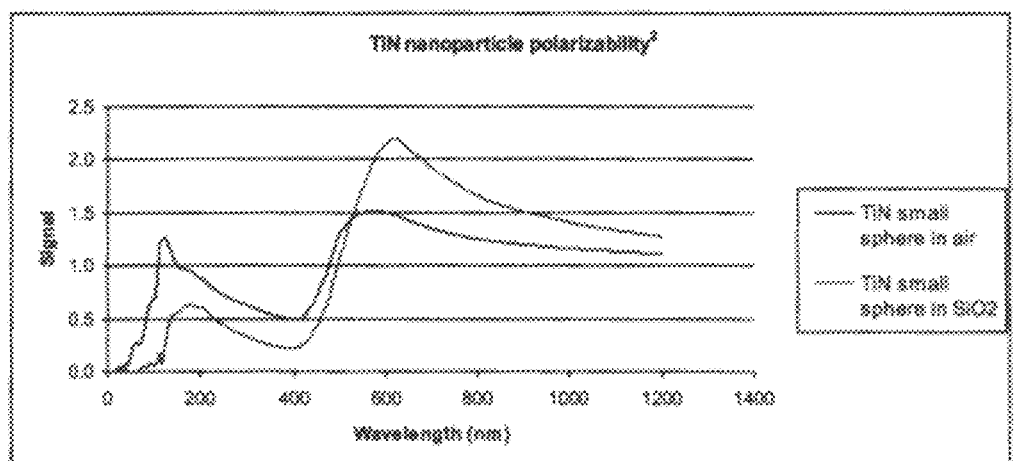
FIG. 4A shows inspection permittivity as a function of inspection wavelength.
Figure 4B:
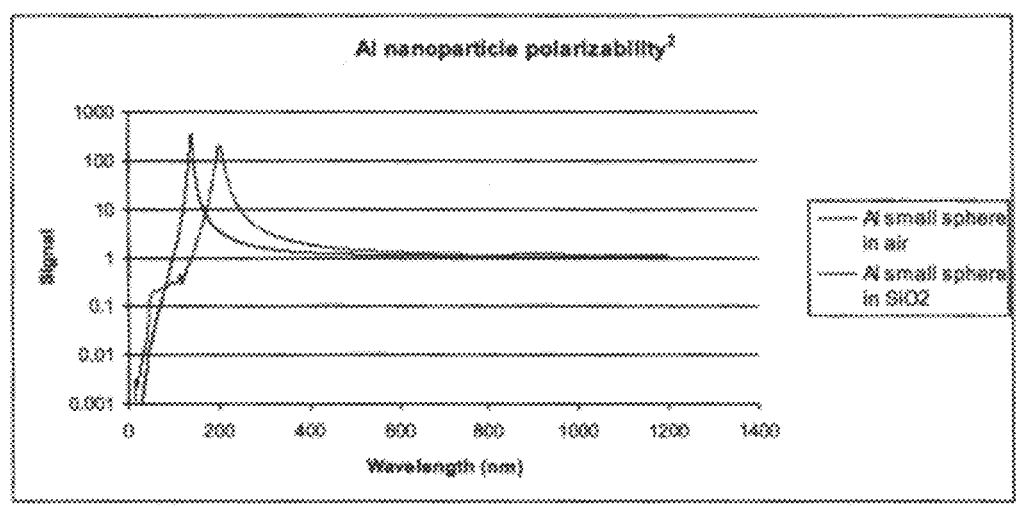
FIG. 4B shows inspection permittivity as a function of inspection wavelength.

A particular topical inspection enhancement layer 103A material may have properties that allow resonant surface plasmons to occur. The potential for such occurrences is a function of the permittivity of the topical inspection enhancement layer 103A. The occurrence of surface plasmon modes for some materials and their use as a component of the topical inspection enhancement layer 103A may be desirable. FIGS. 4A and 4B show scattering cross sections as a function of wavelength where values >1 indicate a potential signal improvement due to a topical inspection enhancement layer 103A. FIG. 4B shows a large potential signal enhancement using a typical noble metal as a topical inspection enhancement layer 103A material having a negative permittivity relative to surrounding material permittivity, a necessary condition to support surface plasmon resonance modes. In contrast, FIG. 4A shows moderate potential signal enhancement from a typical dielectric material that cannot readily support surface plasmon resonance modes.

Figure 5:
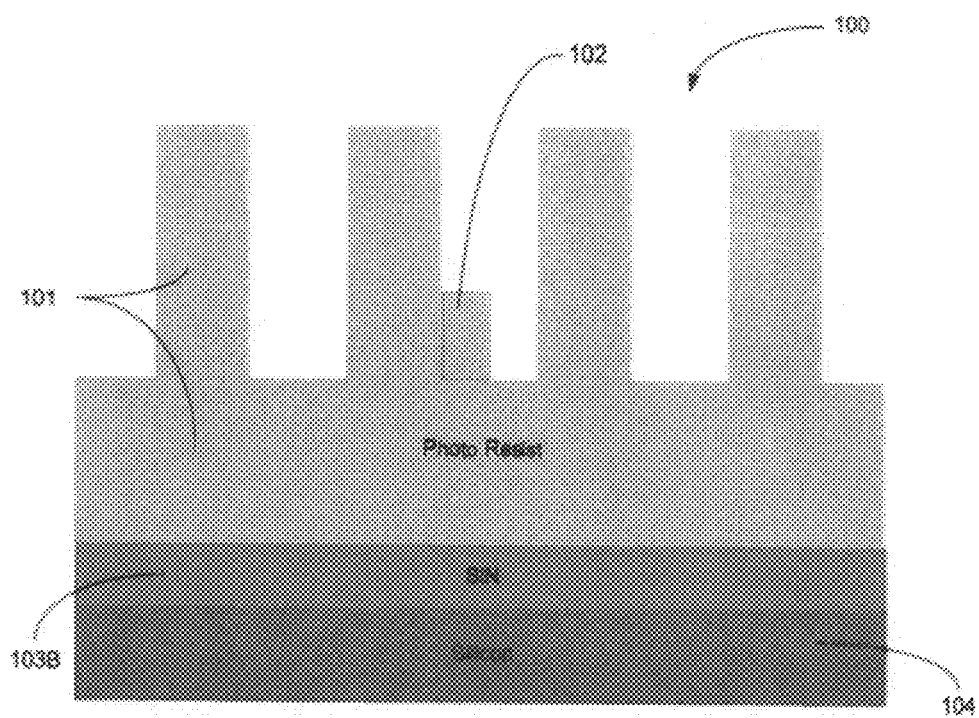
FIG. 5 shows a cross-sectional profile of a wafer surface with a periodic structure and a defect.

Referring to FIG. 5, an inspection target 100 is shown. The inspection target 100 may include at least one inspection enhancement underlayer 103B configured as a transparent underlayer disposed under an inspection layer 101. Such a configuration may result in a thin-film interference effect having an interference maximum at the location of defect structures 102. The thin-film interference can be caused by light reflecting off a substrate 104, and may also reflect off of interlayer boundaries between transparent or semi-transparent materials in the stack (e.g. the boundary between inspection layer 101 and inspection enhancement underlayer 103B) interfering with incident and other reflected light thereby producing standing waves of maximum and minimum electric field intensities. By varying the optical properties (e.g. the refractive index n; the extinction coefficient k) and thickness of the inspection enhancement underlayer 103B, the location of the maximum and minimum electric field within the depth in the inspection layer 101 or other transparent material can be changed and optimized to conform to the inspection wavelength as described below. The inspection target 100 may also include at least one inspection enhancement underlayer 103B configured as a opaque underlayer disposed under an inspection layer 101. In addition to enhancing defect signal, this underlayer may have the added advantage of reducing wafer inspection noise from underlying process variation and previous layer defects.

The inspection layer 101 may be generally applied in a thin layer 40-100 nm thick over a Si blank wafer substrate 104 and then developed for the purpose of testing a stepper tool's focus and exposure or to qualify the mask by inspecting a print-check wafer for mask defects. It may be the case that an optimal wavelength for inspecting such samples may be shorter than current wafer inspection tools utilize. Developing a wafer inspection tool that operates at shorter wavelengths may be costly due to limited and very expensive light sources available, expensive optics and poor optical coating performance, increased risk of photo contamination, wafer damage from high-energy photons to name a few disadvantages. By selecting the material and thickness of the inspection enhancement underlayer 103B, the signal producing properties of the sample may be adjusted such that the maximum inspection wavelengths are moved to within the operating wavelength range for an inspection tool. The interference effect may also be used to maximize the signal by moving the standing wave maximum to the location of the defect. For example, a resulting signal may be a function of the electric field at the defect location and, as such, may change with wavelength of the incident light as the wavelength determines where the maximum and minimum of the standing wave interference will occur. Changing the thickness or material of the underlying layer may alter the interference properties of the stack to maximize the electric field at the defect. This may be done for a particular wavelength or, if a wavelength is known, at a particular location within the structure where the defect is located. It should be noted that such techniques may be used with the other methods to increase signal as well (e.g., the pattern transfer technique as will be discussed below).

Figure 6:
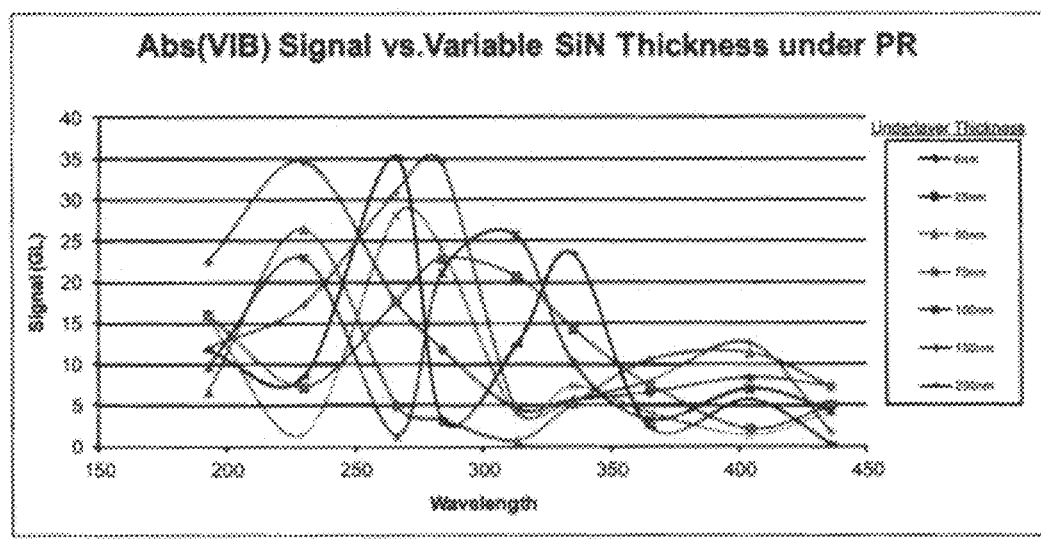
FIG. 6 shows signal responses as a function of wavelength for various inspection enhancement layer thicknesses.

Particularly, the optimum inspection wavelength may be moved to a wavelength range where the potential damage from the inspection photons altering the chemistry of the inspection layer 101 is minimized. To illustrate the effect, a variable thickness SiN inspection enhancement underlayer 103B was simulated beneath an inspection layer 101 and the defect signal in a brightfield low-sigma mode (VIB) from a full-height bridge defect was calculated as a function of the thickness of the SiN inspection enhancement underlayer 103B and inspection wavelength. FIG. 6 shows various signal responses for various inspection enhancement underlayer 103B thicknesses across various wavelengths. As shown in FIG. 6, the uncoated inspection layer 101 may have a maximum wavelength sensitivity at about 230 nm. Such sensitivity may be below inspection thresholds for broadband wafer inspection tools that operate between 260 and 450 nm. As shown, by selecting a depth of 25 nm for the SiN inspection enhancement underlayer 103B, the maximum may be moved to about 300 nm, inside the broadband spectrum and much above the uncoated inspection layer 101 signal. Other thicknesses may be employed to move the signal responses toward other portions of the spectrum that might be advantageous for minimizing noise (which may also be a function of the wavelength) or minimizing wafer damage by photochemical processes.

Figure 7:
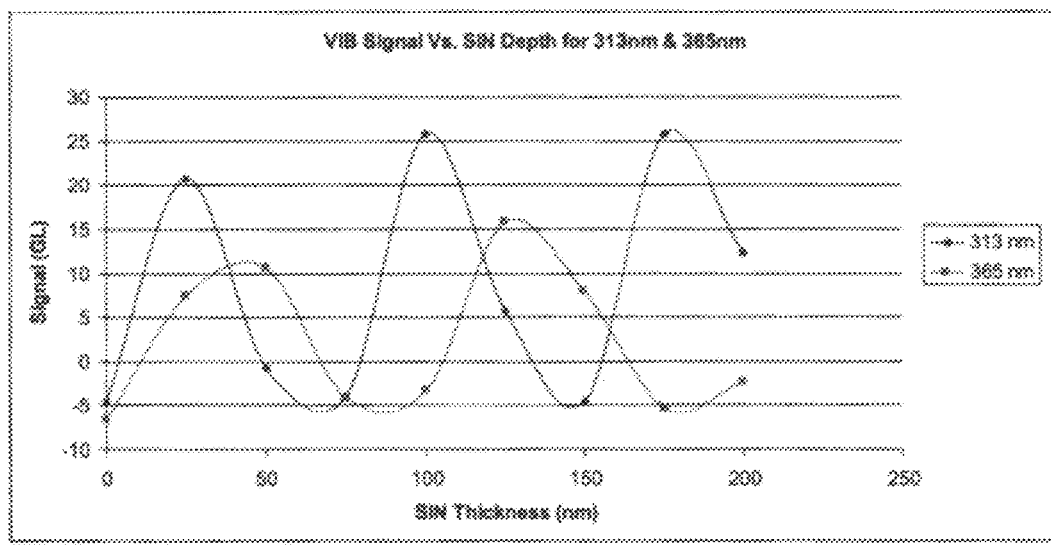
FIG. 7 signal response as a function of the depth of a SiN inspection enhancement layers for 313 nm and 365 nm inspection wavelengths.

If the inspector has a particular light budget maximum at a particular wavelength, the maximum of the defect signal can be tuned to that wavelength by varying the depth and/or material properties (e.g. n, k) of the inspection enhancement underlayer 103B. FIG. 7 illustrates this effect by showing the signal as a function of the depth of a SiN inspection enhancement underlayer 103B for 313 nm and 365 nm. As shown, to obtain a maximum signal response at an inspection wavelength of 365 nm, a SiN inspection enhancement underlayer 103B depth of either about 40 nm or about 140 nm may be selected depending upon which thickness might be better suited to the requirements of other wafer processing steps. It will be recognized that transparent materials other than SiN may be used to create a thin-film interference effect (e.g., SiO2).

Still further, signal response may be improved by transferring a patterned inspection layer 101 of an inspection target 100A onto an inspection enhancement underlayer 103B of a second inspection target 100B. By selecting an inspection enhancement underlayer 103B that has stronger scattering properties, the corresponding defects of the inspection layer 101 may be easier to capture. Such processes are similar to after-etch inspection techniques but are, instead, applied to a short loop wafer (e.g. wafers used to test a particular step in the fabrication process) with one or more under-layer materials that has optimum inspection properties rather than a processed full-loop wafer (e.g. a wafer in a production line). In this way an image pattern and an image of the defect (protrusion, bite, bridge, etc), may be transferred into a material stack with a selected depth, materials and composition. Defect sensitivity may be greater in after-clean inspection (ACI) layers (e.g. as shown in FIG. 8C) than after-develop inspection (ADI) layers (as shown in FIG. 8A). The stack may be designed to exploit material contrast versus wavelength, scattering power of materials (i.e. higher index of refraction), and interference effects as described above. If the wavelengths in a selected inspection band are able to penetrate a stack, the overall volume of the defect scattering center may be increased by increasing defect height. Further, line-space structures (common in photo short loop studies) that have behaved like optical waveguides when the material, dimension, wavelength and incident angle are correctly tuned have been observed. This waveguide effect may be exploited to amplify the E-field in the direct vicinity of the defect of interest.

Referring to FIGS. 8A-8C, a pattern transfer technique for an inspection target 100 is shown. An original pattern of an inspection layer 101 on a silicon substrate 104 of an inspection target 100A (as shown in FIG. 8A) may be patterned on a stack (e.g. a thicker SiN inspection enhancement underlayer 103B with an underlying SiO$_2$ adhesion layer 105 as shown in FIGS. 8B and 8C) of a second inspection target 100B. The inspection layer 101 pattern of the inspection target 100A may be etched into the SiN inspection enhancement underlayer 103B of the second inspection target 100B, and then cleaned prior to inspection (e.g. ACI) to remove etched portions of the SiN topical inspection enhancement layer 103A to leave a patterned inspection enhancement underlayer 103B as shown in FIG. 8C. The patterned inspection enhancement underlayer 103B may then be subjected to inspection.

The patterned inspection enhancement underlayer 103B material may be selected to include a higher scattering material than the inspection layer 101 of inspection target 100A and its thickness and the thickness of an underlying layer (e.g. adhesion layer 105) can be used to move the best signal wavelengths into the range of a wafer inspection tool as described above. Additionally, the depth of the adhesion layer 105 may be similarly adjusted to provide an additional degree of optimization.

Figure 9:
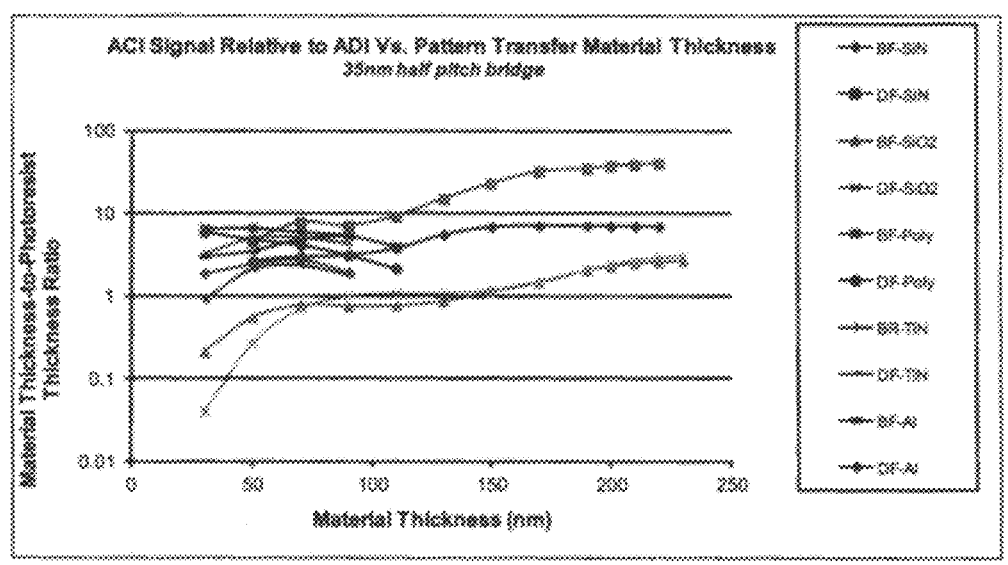
FIG. 9 shows a signal response as a function of patterned inspection enhancement layer thickness for various patterned inspection enhancement layer materials.

Referring to FIG. 9, simulated performance by a 2830 Brightfield Patterned Wafer Defect Inspection System produced by KLA-Tencor Corporation, Milpitas, Calif., on various pattern transfer materials as a function of their thickness is shown. The simulated signals obtained from analysis of an ADI configuration (as shown in FIG. 8A) were used as a normalization factor with the simulated plot signals obtained from an ACI configuration (as shown in FIG. 8C) relative to the ADI for both BF and DF. As shown in FIG. 9, a relatively thick SiN may have the best performance especially in DF where signal increases of >30× are possible. Material choices for the underlayer can include SiN, SiO2, Poly Si, Si, Al, TaN, TiN, and the like.

Figure 10:
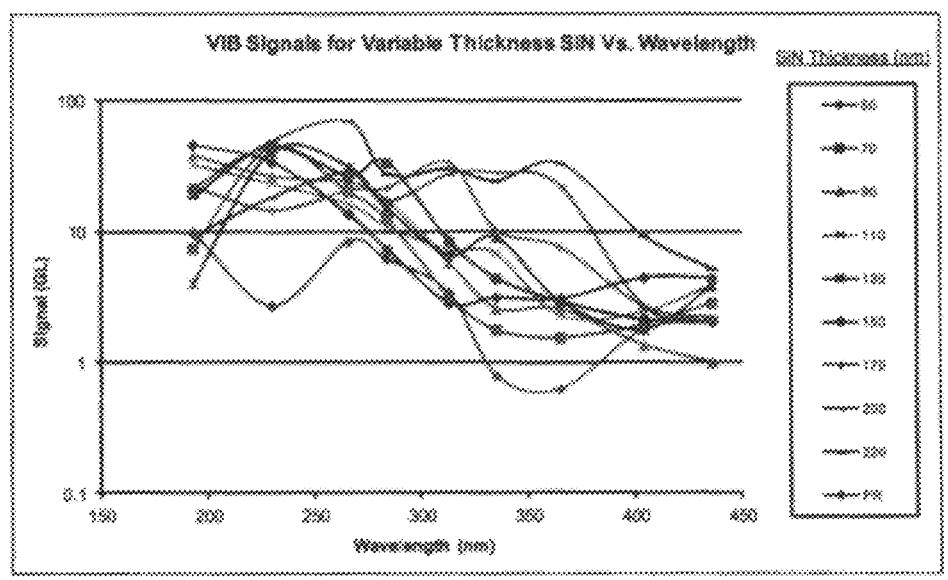
FIG. 10 shows a signal response as a function of inspection wavelength for various inspection enhancement layer thicknesses.

Referring to FIG. 10, the wavelength response for the ACI configuration with various thickness of SiN inspection enhancement underlayer 103B compared with the wavelength response for the ADI configuration without the inspection enhancement underlayer 103B show that the wavelength for enhanced sensitivity may be optimized to correspond with favorable regions by configuring the thickness of the SiN inspection enhancement underlayer 103B. A similar effect can occur by varying the thickness of one or more underlying materials (e.g. adhesion layer 105) to move the best signal to a desired wavelength.

Still further, signal response may be improved by selecting inspection layer 101 materials (e.g. photoresist layers) and/or adding dyes (e.g. to increase absorption) to the inspection layer 101 to enhance optical properties of the inspection layer 101 at inspection wavelengths. By selecting an inspection layer 101 with a refractive index of 1.9, the scattering enhancement can increase by 3.7 compared to a inspection layer 101 with a refractive index of 1.58 over the spectral range of the 2830 Brightfield Patterned Wafer Defect Inspection System produced by KLA-Tencor Corporation, Milpitas, Calif.

Figure 11A:
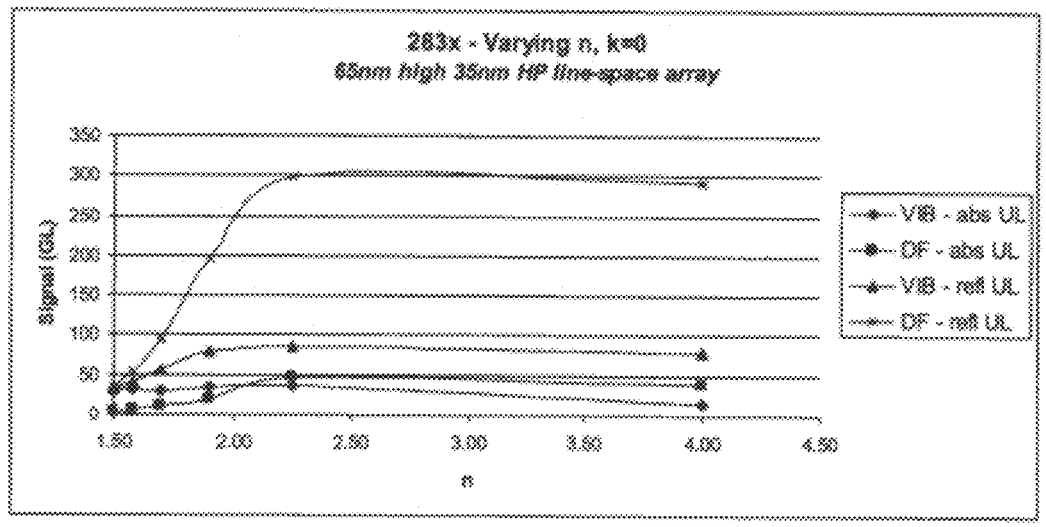
FIG. 11 shows a signal response as a function of resist refractive index n and extinction index k for both reflective and absorptive underlayers.
Figure 11B:
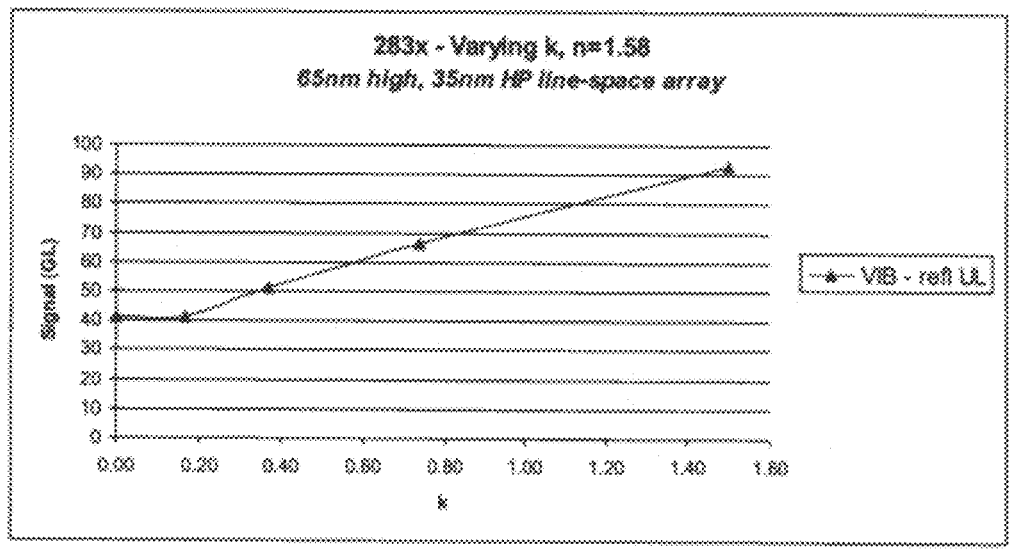

FIG. 11A shows the increase in simulated defect signal as a function of refractive index n at the inspection wavelengths using a darkfield (DF) mode (HPEC) and a brightfield low-sigma mode (VIB) brightfield mode on a 2830 Brightfield Patterned Wafer Defect Inspection System produced by KLA-Tencor Corporation, Milpitas, Calif., and for both reflective and absorptive underlayers. FIG. 11B shows the increase in simulated defect signal in a low-sigma mode (VIB) brightfield mode as a function of extinction coefficient k at the inspection wavelength for a reflective underlayer. By increasing k from 0 to 1.0, the simulated defect signal increases by 1.9×. The extinction coefficient k can be increased at inspection wavelengths by adding dyes whose absorption peaks are centered on the inspection mean wavelength. The refractive index can be increased at inspection wavelengths by selection of inspection layer 101 materials or by adding absorbers with absorption peaks at shorter wavelengths than the inspection wavelengths. The index of refraction naturally increases near the absorption peak for wavelengths longer than the absorption peak (normal dispersion).

The foregoing detailed description has set forth various embodiments of the devices and/or processes via the use of block diagrams, flowcharts and/or examples. Insofar as such block diagrams, flowcharts and/or examples contain one or more functions and/or operations, it will be understood by those within the art that each function and/or operation within such block diagrams, flowcharts or examples can be implemented, individually and/or collectively, by a wide range of hardware, software, firmware or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware may be well within the skill of one of skill in the art in light of this disclosure. In addition, those skilled in the art will appreciate that the mechanisms of the subject matter described herein may be capable of being distributed as a program product in a variety of forms, and that an illustrative embodiment of the subject matter described herein applies regardless of the particular type of signal bearing medium used to actually carry out the distribution. Examples of a signal bearing medium include, but may be not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The herein described subject matter sometimes illustrates different components contained within, or connected with, different other components. It is to be understood that such depicted architectures may be merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but may be not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise. While particular aspects of the present subject matter described herein have been shown and described, it will be apparent to those skilled in the art that, based upon the teachings herein, changes and modifications may be made without departing from the subject matter described herein and its broader aspects and, therefore, the appended claims may be to encompass within their scope all such changes and modifications as may be within the true spirit and scope of the subject matter described herein. It will be understood by those within the art that, in general, terms used herein, and especially in the appended claims (e.g., bodies of the appended claims) may be generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art may understand the convention (e.g., "a system having at least one of A, B, and C" may include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art may understand the convention (e.g., "a system having at least one of A, B, or C" may include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, those skilled in the art will appreciate that recited operations therein may generally be performed in any order. In addition, although various operational flows may be presented in a sequence(s), it should be understood that the various operations may be performed in other orders than those that may be illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to" or other past-tense adjectives may be generally not intended to exclude such variants, unless context dictates otherwise.

Although specific dependencies have been identified in the claims, it is to be noted that all possible combinations of the features of the claims may be envisaged in the present application, and therefore the claims may be to be interpreted to include all possible multiple dependencies. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed is:

1. A method for wafer defect inspection comprising:
providing an inspection target; and
applying at least one topical inspection enhancement layer to at least a portion of the inspection target, the topical inspection enhancement layer including a component exhibiting resonant surface plasmons upon illumination.

2. The method of claim 1, further comprising:
illuminating the inspection target to generate one or more inspection signals associated with one or more features of the patterned inspection target;
detecting the inspection signals;
generating one or more inspection parameters from the inspection signals.

3. The method of claim 1, wherein the topical inspection enhancement layer includes at least one of: titanium nitride, aluminum, silver, gold, tantalum nitride and chromium.

4. The method of claim 1, further comprising:
incorporating one or more materials into one or more inspection layers to modify at least one of a refractive index and an extinction coefficient of the one or more inspection layers at one or more inspection wavelengths.

5. The method of claim 4, wherein the incorporating one or more materials into one or more inspection layers to modify at least one of a refractive index and an extinction coefficient of the one or more inspection layers at one or more inspection wavelengths comprises:

incorporating one or more materials into one or more photoresist inspection layers to modify at least one of a refractive index and an extinction coefficient of the one or more photoresist layers at the one or more inspection wavelengths.

6. The method of claim 5, wherein the incorporating one or more materials into one or more photoresist inspection layers to modify at least one of a refractive index and an extinction coefficient of the one or more photoresist layers at the one or more inspection wavelengths comprises:

adding one or more dyes to the one or more photoresist inspection layers to modify at least one of a refractive index and an extinction coefficient of the one or more photoresist inspection layers at the one or more inspection wavelengths.

7. The inspection target of claim 1, wherein the at least one topical inspection layer comprises:

at least one photoresist layer.

8. The inspection target of claim 7, where in the at least one topical inspection layer comprises:

one or more materials modifying at least one of a refractive index and an extinction coefficient at an inspection wavelength relative to at least one of a refractive index and an extinction coefficient of an inspection layer lacking the one or more materials.

9. The inspection target of claim 1, further comprising:

at least one patterned inspection enhancement underlayer disposed beneath the topical inspection layer.

10. A method for wafer defect inspection comprising:

providing an inspection target; and applying at least one defect inspection enhancement to the inspection target, wherein the applying at least one defect inspection enhancement to the inspection target includes:

disposing one or more inspection enhancement underlayers under at least a portion of one or more layers of the inspection target, wherein the disposing one or more inspection enhancement underlayers under at least a portion of one or more layers of the inspection target includes:

disposing two or more inspection enhancement underlayers including a first inspection enhancement underlayer that absorbs at exposure wavelength and transmits at inspection wavelength and a second inspection enhancement layer that reflects at inspection wavelength to at least a portion of the inspection target beneath an inspection layer of the inspection target.

11. The method of claim 10, wherein the disposing one or more inspection enhancement underlayers under at least a portion of one or more layers of the inspection target where the inspection enhancement underlayer creates a thin-film interference effect comprises:

disposing one or more inspection enhancement underlayers under at least a portion of one or more layers of the inspection target where the inspection enhancement underlayer creates a thin-film interference effect having a maximum intensity at a location of a defect structure.

12. The method of claim 10, further comprising:

configuring at least one of a refractive index of the inspection enhancement underlayer, a coefficient of extinction of the inspection enhancement underlayer and a thickness of the inspection enhancement underlayer to modify resulting inspection signals of the inspection target to correspond to an operating range of an inspection device.

13. The method of claim 10, wherein the disposing one or more inspection enhancement underlayers under at least a portion of one or more layers of the inspection target comprises:

disposing one or more inspection enhancement underlayers including at least one of silicon nitride and silicon dioxide under at least a portion of the inspection target under at least a portion of an inspection layer of the inspection target.

14. A method for wafer defect inspection comprising:

providing an inspection target;

applying at least one defect inspection enhancement to the inspection target;

transferring a patterned inspection layer associated with the inspection target to a second inspection target;

applying at least one inspection enhancement layer to at least a portion of the second inspection target;

applying a patterned photoresist layer corresponding to the patterned inspection layer of the inspection target to the second inspection target over the at least one inspection enhancement layer;

exposing the patterned photoresist layer of the second inspection target; and etching the patterned photoresist layer of the second inspection target photoresist into the at least one inspection enhancement layer of the second inspection target.

15. The method of claim 14, wherein the applying at least one inspection enhancement layer to at least a portion of the second inspection target comprises:

applying at least one inspection enhancement layer including at least one of silicon nitride and poly silicon.

16. The method of claim 14, further comprising:

configuring one or more thicknesses of the inspection enhancement layer to optimize the inspection signals.

* * * * *